United States Patent [19]

Rivier et al.

[11] Patent Number: 5,506,207
[45] Date of Patent: Apr. 9, 1996

[54] GNRH ANTAGONISTS XIII

[75] Inventors: Jean E. F. Rivier, La Jolla; John S. Porter, Leucadia; Carl A. Hoeger, San Marcos; Guangcheng Jiang; Catherine L. Rivier, both of La Jolla, all of Calif.

[73] Assignee: The Salk Institute for Biological Studies, San Diego, Calif.

[21] Appl. No.: 210,627

[22] Filed: Mar. 18, 1994

[51] Int. Cl.$^6$ .............................. A61K 38/04; C07K 7/00
[52] U.S. Cl. ............................................. 514/15; 530/328
[58] Field of Search ............................... 514/15; 530/328

[56] References Cited

U.S. PATENT DOCUMENTS

| | | | |
|---|---|---|---|
| 4,444,759 | 4/1984 | Rivier et al. | 424/177 |
| 4,619,914 | 10/1986 | Vale et al. | 514/15 |
| 5,169,932 | 12/1992 | Hoeger et al. | |
| 5,296,468 | 3/1994 | Hoeger et al. | 514/15 |

OTHER PUBLICATIONS

Dayhoff, Atlas of Protein Sequence and Structure, 1972, vol. 5, (see last page).
Moimas et al., "A New Approach to 1–Nitro–2,2–bis[alkyl–or arylamino]ethylenes: A New Synthesis of Ranitidine", *Communications*, pp. 509–510, May 1985.
Rivier et al., "Novel Linear and Cyclic Gonadotropin Releasing Hormone Antagonists:", 26$^{es}$ Recontres Internationales de Chimie Therapeutique, Univ. of Montpellier, Montpellier, France, Jul. 3–5, 1990.
Rao et al., "Synthesis of cis and trans–4–Aminocyclohexyl–D–Alanine Derivatives and Determination of their Stereochemistry", *Organic Preparations and Procedures Inc.*, 23(1), pp. 103–110, 1991.
Rivier et al., "Gonadotropin Releasing Hormone Antagonists: Novel Structures Incorporating N$^\omega$–Cyano Modified Guanidine Moieties", *Biochemical and Biophysical Research Communications*, vol. 176, No. 1, pp. 406–412, Apr. 15, 1991.
Rivier et al., "Gonadotropin–Releasing Hormone Antagonists with N$^\omega$–Triazolylornithine, –lysine, or –p–aminophenylalanine Residues at Positions 5 and 6", *Journal of Medicinal Chemistry*, pp. 4270–4278, 1992, 35.

Theobald et al., "General Method for Incorporation of Modified N$^\omega$–Cyanoguanidino Moeities on Selected Amino Functions during Solid–Phase Peptide Synthesis", *J. Am. Chem. Soc.*, 112, pp. 9624–9626, 1990.
Theobald et al., "Novel Gonadotropin–Releasing Horomone Antagonists: Peptides Incorporating Modified N$^\omega$–Cyanoguanidino Moieties", *Journal of Medicinal Chemistry*, pp. 2395–2402, 1991, 34.

*Primary Examiner*—Jill Warden
*Assistant Examiner*—Benet Prickril
*Attorney, Agent, or Firm*—Fitch, Even, Tabin & Flannery

[57] ABSTRACT

Analogs of the decapeptide GnRH which include two significantly modified amino acids at positions 5 and 6 inhibit the secretion of gonadotropins by the pituitary gland and inhibit the release of steroids by the gonads. Administration of an effective amount of such GnRH antagonists prevents ovulation of female mammalian eggs and/or the release of steroids by the gonads and may be used to treat steroid-dependent tumors. Particularly effective peptides which are soluble in water at physiologic pH and which have a low tendency to gel when administered in vivo have the following formula:

Ac-β-D-2NAL-(4Cl)D-Phe-D-3PAL-Ser-Aph($Q_1$)(3-amino-1,2,4 triazole)-D-Aph($Q_2$)(3-amino 1,2,4-triazole)-Leu-Lys (isopropyl)-Pro-D-Ala-NH$_2$, where $Q_1$ and $Q_2$ are amino acids, such as Gly, β-Ala, Ala, D-Ala, Ser, Aib, Ahx and Gab. Examples of other GnRH antagonists include Ac-β-D-2NAL-(4Cl)D-Phe-D-3PAL-Ser-Aph(Atz)-D-Aph(Ac)-Leu-Lys(isopropyl)-Pro-D-Ala-NH$_2$, Ac-β-D-2NAL-(4Cl)D-Phe-D-3PAL-Ser-Aph(β-Ala)(3-amino-1,2,4 triazole)-D-Aph(β-Ala)(3-amino-1,2,4 triazole)-Leu-Lys(isopropyl)-Pro-D-Ala-NH$_2$, Ac-β-D-2NAL-(4Cl)D-Phe-D-3PAL-Ser-Aph(Ac-D-Ser)-D-Aph(Ac-D-Ser)-Leu-Lys(isopropyl)-Pro-D-Ala-NH$_2$, and Ac-β-D-2NAL-(4Cl)D-Phe-D-3PAL-Ser-Aph(Ac)-D-Aph(Ac)-Leu-Lys(isopropyl)-Pro-D-Ala-NH$_2$.

15 Claims, No Drawings

GNRH ANTAGONISTS XIII

This invention was made with Government support under grant number HD-13527 and contracts NO1-HD-1-3100 and NO1-HD-0-2906 awarded by the National Institutes of Health. The Government has certain rights in this invention.

This invention relates generally to peptides which are antagonists of human gonadotropin releasing hormone (GnRH) and more particularly to GnRH antagonists that include residues of significantly modified amino acids and that have advantageous physical, chemical and biological properties. In a more particular aspect, the present invention relates to decapeptides which inhibit the gonadal function and the release of the steroidal hormones progesterone and testosterone, and to methods of administering such decapeptides for such purposes and also to prevent ovulation.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH was isolated and characterized as a decapeptide some 20 years ago, and it was found shortly thereafter that analogs of GnRH having a D-isomer instead of Gly in the 6-position, such as [D-Ala$^6$]-GnRH (U.S. Pat. No. 4,072,668) having the following formula:

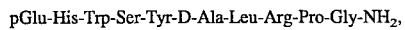

pGlu-His-Trp-Ser-Tyr-D-Ala-Leu-Arg-Pro-Gly-NH$_2$, have greater binding strength to the receptor and greater biological potency than the native hormone.

Peptides are compounds which contain two or more amino acids in which the carboxyl group of one acid is linked to the amino group of the other acid. The formula for [D-Ala$^6$]-GnRH, as represented above, is in accordance with conventional representation of peptides where the amino terminus appears to the left and the carboxyl terminus to the right. The position of each amino acid residue is identified by numbering the amino acid residues from left to right. In the case of GnRH, the hydroxyl portion of the carboxyl group of glycine at the C-terminus has been replaced with an amido group(NH$_2$) i.e. the C-terminus is amidated. The abbreviations for the individual amino acid residues above are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Har is homoarginine, Pro is proline, Sar is sarcosine, Phe is phenylalanine, Ala is alanine, Val is valine, Nva is norvaline, Ile is isoleucine, Thr is threonine, Lys is lysine, Asp is aspartic acid, Asn is asparagine, Gln is glutamine, Cit is citrulline, and Met is methionine. Except for glycine, amino acids of the peptides of the invention are of the L-configuration unless noted otherwise.

There are reasons for desiring to suppress gonadotropin secretions and to prevent ovulation in female mammals, and the administration of GnRH analogs that are antagonistic to the normal function of GnRH have been used for these purposes. For this reason, analogs of GnRH which are antagonistic to GnRH have been investigated for their potential use as a contraceptive, for regulating conception periods, as well as for the treatment of infertility, for the controlled induction of ovulation in women with chronic anovulation, and in in vitro fertilization. They are also useful for the treatment of precocious puberty, endometriosis (including endometriosis with pain), acne, amenorrhea (e.g. secondary amenorrhea), uterine myoma, ovarian and mammary cystic diseases (including polycystic ovarian disease (PCO)) and breast and gynecological cancers. The GnRH antagonists can also be useful in the symptomatic relief of the premenstrual syndrome (PMS). In the female, they can also be used to treat ovarian hyperandrogenism and hirsutism. Such antagonists have also been found useful to regulate the secretion of gonadotropins in male mammals and can be employed to arrest spermatogenesis, e.g. as male contraceptives for treatment of male sex offenders, and for treatment of prostatic hypertrophy. More specifically, GnRH antagonists can be used to treat steroid-dependent tumors, such as prostatic and mammary tumors, and for the control of the timing of ovulation for in vitro fertilization.

The GnRH antagonists can also be used to treat patients suffering from AIDS, rejuvenating the thymus when administered at a dosage of about 10 micrograms/kg/day to 1 mg/kg/day. The thymus then produces T-cells to replace the T-cells destroyed by the AIDS virus, thereby compensating for the effects of the virus.

There are a number of peptides that are known to cause histamine to be released from mast cells which cells are found in the skin, the gingiva and other locations throughout the body. As a result, inflammation is caused, often resulting in edema of the face and elsewhere on the skin. It was earlier found that certain GnRH antagonists that were effective in preventing ovulation had the undesirable adverse side effect of stimulating histamine release, generally rendering such GnRH analogs unacceptable for administration to humans. As a result, the design of GnRH analogs was directed to providing peptides that would retain the biological efficacy but would not have such undesirable histamine release, see J. Rivier et al., *J. Med. Chem.*, 29, 1846–1851 (1986). In addition, it is important that the peptide analog should be well tolerated by the body upon administration, particularly when injected. Preferably, they also have good duration of action upon LH secretion, a property which is considered to be enhanced by resistance to proteolytic enzyme degradation in the body; thus, these properties are also kept in focus in designing new GnRH analogs. In addition, so as to facilitate administration of these compounds to mammals, particularly humans, it is considered advantageous for such GnRH decapeptides to have a high solubility in water, particularly bacteriostatic water, at normal physiologic pH, i.e. from about pH 5 to about pH 7.4.

In J. Rivier et al., *J. Med. Chem.*, 35, 4270–4277 (1992), the design and synthesis of GnRH antagonists having improved properties in various of these respects are described. Despite the attractive properties of these GnRH analogs, the search has continued for still further improved GnRH antagonists, particularly ones that are well-suited to administration by subcutaneous injection and ones that are less expensive to manufacture. All of the GnRH antagonists of interest have at least three D-isomers in their amino acid sequence. Improved GnRH agonists are also desired.

SUMMARY OF THE INVENTION

It has now been found that GnRH antagonist decapeptides having the following formula, and closely related analogs thereof, have particularly advantageous overall properties:

Ac-β-D-2NAL-(4Cl)D-Phe-D-3PAL-Ser-$AA_5$-D-$AA_6$-Leu-Lys(isopropyl)-Pro-D-Ala-$NH_2$, where $AA_5$ and $AA_6$ are residues of amino-substituted phenylalanine (or its equivalent) where the substituent is preferably in the 4-position and is preferably a part of an amide bond to a moiety which is preferably neutral and/or hydrophilic. More preferably the moiety is an acylating agent with 5 carbon atoms or less or one which contains an unsaturated heterocyclic ring containing from 2 to 4 nitrogen atoms, such as a 5-member triazole ring. The residues in the 5- and 6-positions can both have the same substituents, or, for example, the 5-position residue may contain a triazole moiety while the 6-position residue is an amino-substituted Phe (or its equivalent) having its amino substituent acylated, by acetyl or the like. GnRH agonists with similar 6-position residues are also provided.

These antagonists are particularly useful as fertility regulators in humans because they have high biopotency, and many of them are particularly long-acting. They exhibit negligible side effects of stimulating histamine release. They have good solubility in aqueous buffers at physiologic pHs, and they are well tolerated and do not encounter substantial gelling when administered by subcutaneous injection. The presence of an amide bond in the side chain of the 5-position residue and/or in the side chain of the 6-position residue, which bond may link the phenyl group to a heterocyclic ring in certain compounds, is believed to be responsible for the substantial improvement exhibited by these preferred peptides, which may include high solubility and resistance to in vivo gelling. Various of the compounds of this invention also exhibit particularly long-acting biopotency, depressing LH levels of in vivo for as much as 72 hours or more when administered subcutaneously. As a result, these decapeptides find particular use in administration to mammals, especially humans, as fertility regulators and for the treatment of pathological conditions such as precocious puberty, hirsutism, acne, hormone dependent neoplasia, uterine myoma, amenorrhea, dysmenorrhea, endometriosis, PMS, ovarian and mammary cystic diseases, such as PCO, and hormone-dependent tumors, including malignant and benign prostatic, mammary, ovarian and testicular tumors.

These GnRH antagonists are soluble in bacteriostatic water in the physiologic pH range of about 5 to about 7.4; therefore, they can be formulated and administered in concentrated form, particularly at a pH between about 5 and about 7. They are well-tolerated in vivo and are particularly suitable for use in pharmaceutical compositions to be administered by subcutaneous injection. These antagonists are considered particularly effective for the contraceptive treatment of male mammals and for the treatment of steroid-dependent tumors; moreover, many of them are particularly long-acting in their suppression of LH levels following administration and have a particularly low side effect in respect of histamine release.

DETAILED DESCRIPTION OF THE PREFERRED EMBODIMENTS

U.S. Pat. No. 5,169,932, issued Dec. 8, 1992, the disclosure of which is incorporated herein by reference, discloses the design and synthesis of a number of GnRH antagonists wherein the side chains of selected residues are reacted to create cyanoguanidino moieties, some of which subsequently spontaneously convert to a desired heterocycle, e.g. a 3-amino-1,2,4-triazole. The cyanoguanidino moieties in this U.S. patent are built upon an omega-amino group in a side chain of a natural or synthetic α-amino acid, such as lysine, ornithine or amino-substituted phenylalanine (Aph) or an extended chain version thereof, such as amino-substituted homophenylalanine (Ahp). Preferably the amino substitution appears in 4- or para-position on the phenyl ring although it can alternatively be present in the 2- or 3-positions on the ring, which are similarly bioactive; if not specified in the following description, Aph should be understood to be para-substituted. GnRH antagonists having such significantly modified or unnatural amino acids in the 5- and 6-positions have been found to have good biological potency, and it has now been found that, as a result of further modification of the side chains of the 5-position residue and/or the 6-position residue in the decapeptide, particularly advantageous overall properties are obtained.

Over the last decade, the particular properties of each of the 10 residues in the sequence of GnRH, from the standpoint of creating an effective antagonist, have been studied in depth, and as a result of these studies, it has been discovered that there are various equivalent residues that can be chosen and that substitutions of one of these equivalents for another does not significantly detract from the biological potency of the decapeptide GnRH antagonist. The N-terminus is preferably N-acylated. Generally in the 1-position at the N-terminus, it has been shown that an N-acylated D-isomer having an aromatic ring structure in its side chain is suitable, such as substituted D-Phe, substituted or unsubstituted D-Trp, or β-D-Nal, and these 3 residues can generally be interchangeably employed at the N-terminus without substantially altering biological efficacy.

It has also become generally accepted that the inclusion of a para-substituted or a 2,4 chloro-disubstituted or a pentamethyl($Me_5$)D-Phe residue in the 2-position adds significantly to GnRH antagonist activity and that the specific identity of the ring substituent is of only relatively minor importance when selected from among the following: chloro, fluoro, bromo, nitro, methyl and alkoxy.

With respect to the 3-position of the molecule, it has been generally accepted that a D-isomer having an aromatic side chain is preferred, and D-Pal, D-Nal or D-Trp (unsubstituted or with a substitution such as $6NO_2$ or $N^{in}$For) are examples that may be employed without significantly changing biological antagonist activity, with D-Pal being preferred. Although there are tolerable equivalents for serine in the 4-position which have been disclosed, such have not significantly improved biological activity, and the native residue is generally preferred in this position.

It is disclosed in U.S. Pat. No. 4,652,550, issued Mar. 24, 1987, that a number of substitutions can be made for Leu in the 7-position without significantly detracting from biological potency, and these potential substituents are now considered to be equivalents. However, Leu or $N^\alpha CH_3$Leu(NML) has most frequently been used, and either of these two or Nle or Phe is generally preferred. In the 8-position, the naturally-occurring residue Arg can be employed, or one of the following residues: Har, Arg or Har which are substituted by diethyl, isopropyl lysine (ILys) and isopropyl ornithine (IOrn), which are considered to be equivalents for this position, with ILys being generally preferred. In the 9-position, the native residue Pro is preferred; however, N-methylalanine can be used as an equivalent. Although the amidated residue Gly can be employed at the C-terminus as in the native hormone, D-alanine having its alpha-carboxyl group amidated is preferred. Other equivalents either use AzaGly-NH$_2$, or omit the 10-position residue and instead use the ethylamide of proline in the 9-position.

In view of the foregoing, the present invention is broadly considered to provide a family of GnRH antagonists represented by the following formula:

G-AA$_1$-(A)D-Phe-AA$_3$-Ser-AA$_5$-D-AA$_6$-AA$_7$-AA$_8$-Pro-AA$_{10}$ wherein G is an acyl group having 7 or less carbon atoms; AA$_1$ is β-D-NAL, (A)D-Phe or(B)D-Trp; A is Cl, F, NO$_2$, Br, CH$_3$, OCH$_3$, Me$_5$ or Cl$_2$; B is H, NO$_2$, OCH$_3$, F, Cl, Br, CH$_3$ or N$^{in}$For; AA$_3$ is D-PAL, β-D-NAL or (B)D-Trp; AA$_7$ is Leu, NML, Nle, Phe, Met, Nva, Tyr, Trp or PAL; AA$_8$ is ILys, (C)Arg, (C)Har or IOrn; C is H or di-lower alkyl; AA$_{10}$ is D-Ala-NH$_2$, Gly-NH$_2$, AzaGly-NH$_2$ or NH(R$_2$); R$_2$ is lower alkyl, preferably CH$_2$CH$_3$. Each of AA$_5$ and AA$_6$ can independently be a modified Phe residue having a substitution in the phenyl ring, preferably at the 4-position. Either AA$_5$ or AA$_6$ or both includes an amide bond by which a neutral and/or hydrophilic moiety is connected to the phenyl ring. The moiety which is so connected may include an unsaturated nitrogen-containing ring, preferably

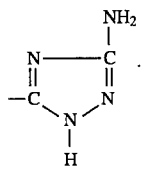

When the 5-position residue contains this preferred triazole moiety, either with or without an amide bond in the connecting linkage, the Phe 6-position residue may be substituted, for example, with an amino group that has been acylated, with the acyl group being one having 5 or less carbon atoms such as formyl (For), acetyl (Ac), acrylyl (Acr), propionyl (Pr), butyryl (Bt) and valeryl, which may be substituted by halogen or hydroxy, e.g. chloroacetyl (Cac) or hydroxyacetyl (Hac). Alternatively, both AA$_5$ and AA$_6$ may be so constituted.

By β-D-NAL is meant the D-isomer of alanine which is substituted by naphthyl on the β-carbon atom, i.e., also 3-D-NAL. Preferably β-D-2NAL is employed wherein the attachment to naphthalene is at the 2-position on the ring structure; however, β-D-1NAL may also be used. The preferred 1-position residues are β-D-NAL, substituted D-Phe and optionally substituted D-Trp; 3,4 dehydroproline, C$_5$H$_7$O$_2$N however, is considered an equivalent. PAL represents alanine which is substituted by pyridyl on the β-carbon atom; preferably the linkage is to the 3-position on the pyridine ring. When substituted D-Trp is employed, single substitutions for hydrogen are preferably made in either the 5- or 6-position, which are selected from chloro, fluoro, bromo, methyl, amino, methoxy and nitro, with chloro, fluoro and nitro being preferred. Alternatively, the indole nitrogen may be acylated with formyl (N$^{in}$For- or 1For-). D-3PAL, N$^{in}$For-D-Trp and 6NO$_2$-D-Trp are the preferred residues for the 3-position although β-D-2Nal and D-Trp are also often used. By NML is meant N$^α$CH$_3$-L-Leu. By Aph is meant 4NH$_2$Phe; unless otherwise specified, the amino substitution should be understood to be in the 4-position. By Ahp is meant NH$_2$-homophenylalanine, which is considered an equivalent to Aph. By AzaGly-NH$_2$ is meant NHNHCONH$_2$. The 7-position residue is preferably Leu, NML, Nle or Phe, and the 8-position residue is preferably ILys.

Other abbreviations which appear herein with respect generally to moieties used in modifying the side chains of the residues in the 5- and 6-positions are set forth hereinafter. By Gab is meant gamma-amino butyric acid. By Aib is meant 2-aminoisobutyric acid. By Cit is meant Citrulline, C$_6$H$_{13}$N$_3$O$_3$, carbamyl ornithine. By Iac is meant imidazole acetic acid. By Ura is meant urocanic acid. By Iop is meant imidazole propionic acid. By Atc is meant aminotriazole carboxylic acid. By Pca is meant 2-pyrazine carboxylic acid. By Apc is meant 3-amino-4-pyrazole carboxylic acid. By Ahx is meant 6-amino-hexanoic acid. When it is recited that an amino group is blocked, it is meant that it is modified so it is no longer a primary amino group, as by acylation to an amido group.

A preferred subgenus of GnRH antagonists has the formula:

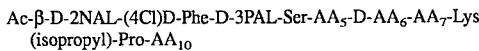

Ac-β-D-2NAL-(4Cl)D-Phe-D-3PAL-Ser-AA$_5$-D-AA$_6$-AA$_7$-Lys (isopropyl)-Pro-AA$_{10}$ wherein AA$_7$ is Leu or N$^α$CH$_3$Leu; AA$_{10}$ is D-Ala-NH$_2$, Gly-NH$_2$, NHCH$_2$CH$_3$ or AzaGly; AA$_5$ is Aph(Q$_1$) (atz); AA$_6$ is Aph(Q$_2$) (atz); atz is

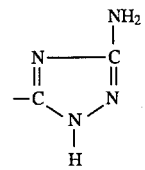

and Q$_1$ and Q$_2$ are independently alpha-amino acids preferably having neutral side chains which are relatively hydrophilic such as Gly, Ser, Thr, Tyr, Asn, pGlu and Gln, which may be in the L- or D-isomer form.

Another preferred subgenus of GnRH antagonists has the formula:

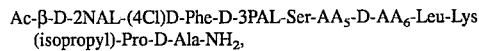

Ac-β-D-2NAL-(4Cl)D-Phe-D-3PAL-Ser-AA$_5$-D-AA$_6$-Leu-Lys (isopropyl)-Pro-D-Ala-NH$_2$, wherein AA$_5$ and AA$_6$ are independently residues of Aph or Ahp linked by an amide bond to an amino acid, such as Gly, β-Ala, Ala, D-Ala, Ser, Ahx and Gab, which is modified so that its amino group is substituted by a triazole moiety. One such subgenus includes the following modified α-amino acids:

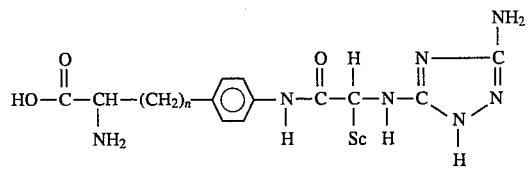

wherein n is 1 or 2 and preferably is 1, and SC is a neutral and/or hydrophilic side chain. For purposes of this application, an amino acid having an isoelectric point (pI) of between about 4 and about 9 is considered to have a neutral side chain.

An additional preferred subgenus of GnRH antagonists has the formula:

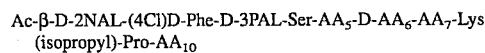

Ac-β-D-2NAL-(4Cl)D-Phe-D-3PAL-Ser-AA$_5$-D-AA$_6$-AA$_7$-Lys (isopropyl)-Pro-AA$_{10}$ wherein AA$_5$ is Aph(Q$_3$);,AA$_6$ is Aph(Q$_4$); AA$_7$ is Leu or NML; $AA_{10}$ is D-Ala-$NH_2$, Gly-$NH_2$, $NHCH_2CH_3$ or Aza-Gly; and $Q_3$ and $Q_4$ are independently alpha-amino acids preferably having neutral side chains which are relatively hydrophilic, such as Gly, Ser, Thr, Tyr, His, Cit, Asn and Gln, the alpha-amino group of which is acylated, which may be in the L- or D-isomer form.

Still another preferred subgenus of GnRH antagonists has the formula:

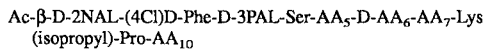

wherein $AA_5$ is Aph($Q_3$); $AA_6$ is Aph($Q_4$); $AA_7$ is Leu or NML; $AA_{10}$ is D-Ala-$NH_2$, Gly-$NH_2$, $NHCH_2CH_3$ or Aza-Gly; and $Q_3$ and $Q_4$ independently comprise heterocyclic ring moieties having from 2 to 4 nitrogen atoms that are connected to the phenyl ring by a linkage which includes an amide bond.

One more preferred subgenus of GnRH antagonists has the formula:

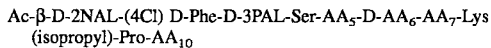

wherein $AA_5$ is Aph($Q_3$); $AA_6$ is Aph($Q_4$); $AA_7$ is Leu or NML; $AA_{10}$ is D-Ala-$NH_2$, Gly-$NH_2$, $NHCH_2CH_3$ or Aza-Gly; and $Q_3$ and $Q_4$ independently comprise substituted or unsubstituted acyl groups which are linked by an amide bond to the amino substituent and which have the formula —$CO(CH_2)_mCH_2X$ where m is 0, 1, 2 or 3 and X is H, Cl, F, Br or I.

Another preferred subgenus which has long-acting properties has the formula Ac-β-D-2NAL-(4Cl)D-Phe-D-3PAL-Ser-$AA_5$-D-$AA_6$-Leu-Lys(isopropyl)-Pro-D-Ala-$NH_2$, wherein $AA_5$ is Aph(atz) and wherein $AA_6$ is Aph(E) where E is an acyl group as defined just above.

The peptides of the present invention can be synthesized by classical solution synthesis, but are preferably synthesized by a solid phase technique. A chloromethylated resin or a hydroxymethylated resin may be used; however, a methylbenzhydrylamine(MBHA) resin, a benzhydrylamine (BHA) resin or some other suitable resin known in the art which directly provides a C-terminal amide or substituted amide upon cleavage is preferably employed. For example, peptides having a substituted amide at the C-terminus are preferably synthesized using an N-alkylamino methyl resin as taught in U.S. Pat. No. 4,569,967, issued Feb. 11, 1986. Solid phase synthesis is conducted in a manner to stepwise add amino acids in the chain in the manner set forth in detail in the U.S. Pat. No. 4,211,693. Side-chain protecting groups, as are well known in the art, are preferably included as a part of any amino acid which has a particularly reactive side chain and optionally in the case of others, such as Trp, which amino acids are to be coupled in the chain being built upon the resin. Such synthesis provides the fully protected intermediate peptidoresin.

Chemical intermediates made generally in accordance with the invention may be represented by the formula:

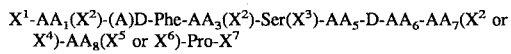

wherein $X^1$ is an α-amino protecting group of the type known to be useful in the art in the stepwise synthesis of polypeptides. When G in the desired peptide composition is a particular acyl group, it may be appropriate to employ such group as the protecting group. Among the classes of α-amino protecting groups covered by $X^1$ are (1) acyl-type protecting groups, such as formyl(For), trifluoroacetyl, phthalyl, p-toluenesulfonyl(Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxycarbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc.

$X^2$ is hydrogen or a protecting group for the indole nitrogen of Trp, such as Bz, Ac or For. In many syntheses there is no need to protect Trp, and such protection is not used if acylated D-Trp is present elsewhere in the peptide.

$X^3$ is hydrogen or a protecting group for the hydroxyl side chain of Ser, e.g. Ac, Bz, trityl, DCB or benzyl ether(Bzl) and is preferably Bzl.

$X^4$ is hydrogen or a protecting group for the phenolic hydroxyl group of Tyr selected from the group consisting of tetrahydropyranyl, tert-butyl, trityl, benzyl, Z, 2-bromobenzyloxycarbonyl(2BrZ) and 2,6-dichlorobenzyl(DCB). 2BrZ is preferred.

Met, if used, may be protected by oxygen, but Met is generally left unprotected.

$X^5$ is a protecting group for a side chain guanidino group in Arg or Har, such as nitro, Tos, trityl, adamantyloxycarbonyl, Z and 2,4-dinitrophenol(Dnp), or $X^5$ may be hydrogen, which means there is no protection on the side chain group atoms. Tos is generally preferred.

$X^6$ is a protecting group for an amino side chain group, primary or secondary amino, such as Z or 2ClZ.

$X^7$ may be Gly-NH-[resin support], D-Ala-NH-[resin support] or N(A)-[resin support]; $X^7$ may also be an amide either of Gly or of D-Ala or a substituted amide attached directly to Pro or $NHNHCONH_2$.

The criterion for selecting certain side chain protecting groups for $X^2$–$X^6$ is that the protecting group should be stable to the reagent under the reaction conditions selected for removing the α-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. Other protecting groups initially employed for the 5- and 6-position residues are removed prior to cleavage from the resin, as explained hereinafter.

When the $X^7$ group is Gly-NH-[resin support] or D-Ala-NH-[resin support], an amide bond connects Gly or D-Ala to a BHA resin or to a MBHA resin. When the $X^7$ group is N(A)-[resin support], a substituted amide bond connects Pro to an N-alkylaminomethyl (NAAM) resin. When $X^7$ is AzaGly-$NH_2$, the peptide is preferably made by classical solution synthesis, as disclosed in U.S. Pat. No. 4,234,571.

When G is acetyl, for example, in the final formula, it may be possible to employ it as the $X^1$ protecting group for the α-amino group of β-D-NAL or whatever amino acid is used in the 1-position by adding it before coupling this last amino acid to the peptide chain. However, a reaction is preferably carried out with the peptide on the resin (after deblocking the α-amino group while the side-chain groups remain protected), e.g. by reacting with acetic acid, or preferably with acetic anhydride, in the presence of diisopropyl or dicyclohexyl carbodiimide (DIC or DCC) or by some other suitable reaction as known in the art.

Thus, the invention also provides a method for making a GnRH peptide having the formula:

wherein $AA_1$, $AA_3$, $AA_5$, $AA_6$, $AA_7$, $AA_8$ and $AA_{10}$ are as set forth hereinbefore, which method comprises (a) forming an intermediate peptide having the formula:

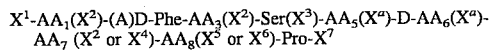

wherein $X^1$ is hydrogen or an α-amino protecting group; $X^2$ is hydrogen or a protecting group for an indole nitrogen; $X^3$ is a protecting group for a hydroxyl group of Ser; $X^4$ is hydrogen or a protecting group for a phenolic hydroxyl group of Tyr; $X^5$ is either hydrogen or a protecting group for a guanidino side chain; $X^6$ is a protecting group for an amino side chain, of which $X^a$ is a subgroup that is removable without removing other protecting groups; $X^7$ is Gly-NH-[resin support], D-Ala-NH-[resin support], N(A)-[resin support], an amide either of Gly or of D-Ala or a substituted amide attached directly to Pro or $NHNHCONH_2$; (b) removing $X^a$ from $AA_5$ and $AA_6$ to deprotect a side chain primary amino group of these amino acid residues of said intermediate peptide; (c) reacting said deprotected side chain primary amino groups to build each said residue into one having the modified side chain desired; and (d) splitting off any remaining groups $X^1$ to $X^6$ and/or cleaving from any resin support included in $X^7$.

Purification of the peptide is effected by ion exchange chromatography on a CMC column, followed by partition chromatography using the elution system: n-butanol;0.1N acetic acid (1:1 volume ratio) on a column packed with Sephadex G-25, or by using HPLC, as known in the art and specifically set forth in J. Rivier, et al. *J. Chromatography*, 288 (1984) 303–328.

The antagonists of the invention are effective at levels of less than 100 micrograms per kilogram of body weight, when administered subcutaneously at about noon on the day of proestrus, to prevent ovulation in female rats. For prolonged suppression of ovulation, it may be necessary to use dosage levels in the range of from about 0.1 to about 2.5 milligrams per kilogram of body weight. These analogs are particularly soluble at physiological pHs and thus can be prepared as relatively concentrated solutions for administration, particularly for subcutaneous injection. These peptides are well tolerated in the body and do not exhibit a tendency to gel and remain at the point of injection when administered subcutaneously. The antagonists are also effective to arrest spermatogenesis when administered to male mammals on a regular basis and can thus be used as contraceptives. Since these compounds will reduce testosterone levels (an undesired consequence in the normal, sexually active male), it may be desirable to administer replacement dosages of testosterone along with the GnRH antagonist. These antagonists can also be used to regulate the production of gonadotropins and sex steroids for other purposes as indicated hereinbefore.

In the following formulas, the residues for positions 5 and 6 are sometimes defined in terms of the original amino acid residue having a side chain amino group plus the modification in question which is set forth in the accompanying parentheses. Preferably, the original residue is incorporated in the main peptide chain, for example Aph or Ahp or the respective D-isomer thereof, and is modified to form the desired residue $AA_5$ or $AA_6$ while a part of the peptide chain that is still attached to the resin. However, a suitably protected, significantly modified amino acid can alternatively be added to the growing peptide chain as a part of the usual chain elongation process, if desired.

The following Examples illustrate a number of GnRH antagonist peptides embodying various features of the invention. All of these peptides include at least one D-isomer amino acid residue. The modifications of the amino acids included in the 5- and 6-positions are preferably made subsequently to the linkage of each to the peptidoresin (as described below).

EXAMPLE 1

The decapeptide [Ac-β-D-2NAL$^1$, (4Cl)D-Phe$^2$, D-3PAL$^3$, Aph(Gly)(atz)$^5$, D-Aph(Gly)(atz)$^6$, ILys$^8$, D-Ala$^{10}$]-GnRH Peptide No. 1 is synthesized by solid-phase synthesis. This peptide has the following formula:

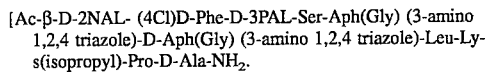

About 3 grams (0.76 mM/g) of MBHA resin are used, and Boc-protected D-Ala is coupled to the resin over a 2-hour period in $DMF/CH_2Cl_2$ using about 5 millimoles of Boc derivative and dicyclohexylcarbodiimide (DCC) as an activating reagent. The D-Ala residue attaches to the MBHA residue by an amide bond.

Following the coupling of each amino acid residue, washing, deblocking and coupling of the next amino acid residue is carried out in accordance with the following schedule using an automated machine and beginning with about 1.5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50% TFA plus 5% 1,2 ethanedithiol in $CH_2Cl_2$-70 ml. (2 times) | 10 |
| 5 | Isopropyl alcohol + 1% ethanedithiol wash-80 ml. (2 times) | 3 |
| 6 | TEA 12.5% in $CH_2Cl_2$-70 ml. | 5 |
| 7 | MeOH wash-40 ml. (2 times) | 2 |
| 8 | TEA 12.5% in $CH_2Cl_2$-70 ml. (2 times) | 2 |
| 9 | $CH_2Cl_2$ wash-80 ml. (3 times) | 3 |

-continued

| STEP | REAGENTS AND OPERATIONS | MIX TIMES MIN. |
|------|-------------------------|----------------|
| 10 | Boc-amino acid (5 remoles) in 30 ml. of either dimethylformamide(DMF):$CH_2Cl_2$ or N-methylpyrrolidinone(DMP):DCM, depending upon the solubility of the particular protected amino acid, plus DIC or DCC (5 remoles) in $CH_2Cl_2$ | 30–300 |
| 11 | MeOH wash-40 ml. (2 times) | 3 |
| 12 | Triethylamine(TEA) 12.5% in $CH_2Cl_2$-70 ml. | 3 |
| 13 | MeOH wash-30 ml. (2 times) | 3 |
| 14 | DCM wash-80 ml. (2 times) | 3 |

The above schedule is used for coupling of each of the amino acids of the peptide of the invention after the first amino acid has been attached. $N^\alpha$Boc protection is used for each of the remaining amino acids throughout the synthesis. $N^\alpha$Boc-β-D-2NAL is prepared by a method known in the art, e.g. as described in detail in U.S. Pat. No. 4,234,571, issued Nov. 18, 1980; it is also commercially available from SyntheTech, Oregon, U.S.A. The side chain primary amino groups of Aph in the 5-position and of D-Aph in the 6-position are protected by Fmoc. Bzl(benzyl ether) may be used as a side chain protecting group for the hydroxyl group of Ser, or Ser may be coupled without side chain protection. Boc-Lys(Ipr,Z) is used for the 8-position residue. After deblocking the α-amino group at the N-terminus using trifluoroacetic acid (TFA), acetylation is achieved using a large excess of acetic anhydride in dichloromethane.

Following completion of the assembly of the peptide and acetylation of the N-terminus, about 9 grams of the following intermediate are present:

Ac-β-D-2NAL-(4Cl)D-Phe-D- 3PAL-Ser(Bzl)-Aph(Fmoc)-D-Aph-(Fmoc)-Leu-Lys(Ipr,Z)-Pro-D-Ala-NH-[ MBHA resin support].

The side chains on the amino acid residues in the 5- and 6-positions are then modified by simultaneously carrying out the following reactions after deprotecting the side chains of the Aph residues. The Fmoc protecting group is removed from both residues by treatment of about 400 mg. of the peptidoresin with 20 percent piperidine in DMF(10 ml.) for about 30 minutes; it is preferably washed with DMF and then treated with more piperidine/DMF for another 30 minutes. After preferably washing the peptidoresin with DMF, the newly freed amino groups are treated with Boc-Gly( 2.5 eq.) in 5 ml. of DMF and 2.5 eq. of diisopropylcarbodiimide (DIC), stirring overnight. The Boc protecting group of Gly is removed by treatment with 50% TFA in 10 ml. of DCM for 30 minutes. Diphenyl cyanocarbonimidate (PCI)(2.5 eq.) in 5 ml. of DMF is reacted with the resin peptide by stirring overnight at room temperature. Thereafter, the peptide resin is subjected to the standard wash and then treated with hydrazine (3 ml. in DMF)(3 ml.) overnight at room temperature to complete the formation of the cyanoguanidino moiety at the alpha-amino group of the Gly residues. This step is preferably repeated. The cyanoguanidino moieties that are formed spontaneously convert to the corresponding heterocycle, i.e. 3-amino- 1,2,4-triazole. The peptide resin is then subjected to the standard wash.

The peptidoresin is dried, and then cleavage of the peptide from the resin and deprotection of the Ser and the Lys side chains is carried out at 0° C. with HF for about 40 min. Anisole is added as a scavenger prior to HF treatment. After the removal of HF under vacuum, the resin is washed twice with 100 ml. of ethyl ether. The cleaved peptide is extracted from the resin with equal parts of $CH_3CN$ and $H_2O$, repeating the process and using 100 ml. each time. The extracts are pooled and lyophilized, and they provide about 181 mg of a crude peptide powder.

Purification of the peptide is then effected by preparative high performance liquid chromatography (HPLC), as known in the art and specifically set forth in J. Rivier, et al. *J. Chromatography*, 288, 303–328 (1984). The first preparative RP-HPLC separation uses a TEAP (triethylammonium phosphate) buffer system. This separation is repeated using the same buffer system with a slightly different gradient, and the final separation is carried out using a 0.1% TFA (trifluoroacetic acid) gradient, all as described in detail in the *J. Chromatography* article. About 92 milligrams of the decapeptide are obtained.

The peptide is judged to be homogeneous using capillary zone electrophoresis (CZE), as well as by using reversed-phase high pressure liquid chromatography and an aqueous triethylammonium phosphate buffer plus acetonitrile. The purity is estimated to be about 97%– 98%. Amino acid analysis of the resultant, purified peptide is consistent with the formula for the prepared structure, showing substantially integer-values for each amino acid in the chain; mass spectral analysis is also consistent. The optical rotation is measured on a photoelectric polarimeter as $[\alpha]_D^{20}=-34°\pm1.0(c=1, 50\%$ acetic acid).

The peptide is assayed in vivo to determine its effectiveness to prevent ovulation in female rats. In this test, a specified number of mature female Sprague-Dawley rats, e.g. five to ten, each having a body weight from 225 to 250 grams, are injected with a specified microgram dosage of the peptide in bacteriostatic water at about noon on the day of proestrus. Proestrus is the afternoon of ovulation. A separate female rat group is used as a control to which the peptide is not administered. Each of the control female rats ovulates on the evening of proestrus; the number of the rats treated which ovulate is recorded. In vivo testing of the peptide shows that, at a dosage of 0.5 micrograms, 3 out of 4 rats treated ovulate, and at a dosage of 1 microgram, only 5 out of 8 rats ovulate. Examination of the rats shows that the peptide was very well tolerated with no significant gelling at the point of injection being detectable.

In vitro testing is carried out using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydro Pro[1], (4F)D-Phe[2], D-Trp[3,6]]-GnRH or the test peptide, in concentrations ranging from 0.01 to 10 nanomolar. The amount of LH secreted in the samples treated only with GnRH is compared with that secreted by the samples treated with the peptide plus GnRH. The peptide is more potent than the present standard [Ac-Δ³Pro¹, D-4FPhe², D-Trp³,⁶]-GnRH.

The peptide is considered to be particularly useful because of its solubility in aqueous buffers at a pH of from about 5 to about 7 and its resistance to in vivo gelling which renders it particularly suitable for administration by subcutaneous injection compared to other compounds of generally comparable biological efficacy. Moreover, it exhibits fairly long-acting biopotency, suppressing LH concentrations to levels that are less than 20% of starting levels for more than 48 hours.

EXAMPLE 2

The following peptides indicated in TABLE A, having the general formula:

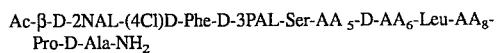

Ac-β-D-2NAL-(4Cl)D-Phe-D-3PAL-Ser-AA₅-D-AA₆-Leu-AA₈-Pro-D-Ala-NH₂ are prepared by the solid-phase procedure generally referred to above in Example 1 but substituting the appropriate amino acid(s).

TABLE A

| No. | AA₅ | AA₆ | AA₈ |
|---|---|---|---|
| 2 | Aph(β-Ala)(atz) | D-Aph(β-Ala)(atz) | ILys |
| 3 | Aph(Gab)(atz) | D-Aph(Gab)(atz) | " |
| 4 | Aph(Ala)(atz) | D-Aph(Ala)(atz) | " |
| 5 | Aph(D-Ala)(atz) | D-Aph(D-Ala)(atz) | ILYS |
| 6 | Aph(Ahx)(atz) | D-Aph(Ahx)(atz) | " |
| 7 | Aph(Aib)(atz) | D-Aph(Aib)(atz) | Arg |
| 8 | Aph(Ala)(atz) | D-Aph(Ala)(atz) | Har |
| 9 | Aph(Aib)(atz) | D-Aph(Aib)(atz) | Arg |
| 10 | Aph(Ser)(atz) | D-Aph(Ser)(atz) | ILys |
| 11 | Ahp(Gly)(atz) | D-Ahp(Gly)(atz) | IOrn |
| 12 | Aph(Asn)(atz) | D-Aph(Asn)(atz) | Arg |
| 13 | Aph(Gln)(atz) | D-Aph(Gln)(atz) | Arg |
| 14 | Ahp(His)(atz) | D-Ahp(His)(atz) | Har |

By atz is meant 3-amino, 1,2,4 triazole.

The peptides listed in Table A are considered effective to block GnRH-induced LH secretion in vitro at a reasonable concentration. All of the peptides are considered to be effective to prevent ovulation of female mammals at low dosages. Testing for duration of effectiveness shows that Peptide No. 2 exhibits very long duration, suppressing LH secretion to a level of less than about 20% of original concentration in peripheral serum for more than 72 hours.

EXAMPLE 3

Peptides as indicated in TABLE B having the formula:

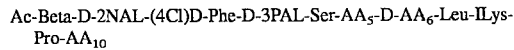

Ac-Beta-D-2NAL-(4Cl)D-Phe-D-3PAL-Ser-AA₅-D-AA₆-Leu-ILys-Pro-AA₁₀ are prepared using the overall solid-phase procedure generally referred to in Example 1 using an appropriate resin as known in this art.

TABLE B

| No. | AA₅ | AA₆ | AA₁₀ |
|---|---|---|---|
| 15 | Aph(pGlu) | D-Aph(pGlu) | D-Ala—NH₂ |
| 16 | Aph(Ser) | D-Aph(Ser) | " |
| 17 | Aph(Ac—Ser) | D-Aph(Ac—Ser) | " |
| 18 | Aph(D-Ser) | D-Aph(D-Ser) | " |
| 19 | Aph(Ac—D-Ser) | D-Aph(Ac—D-Ser) | " |

TABLE B-continued

| No. | AA₅ | AA₆ | AA₁₀ |
|---|---|---|---|
| 20 | Aph(Ac—D-His) | D-Aph(Ac—D-His) | " |
| 21 | Aph(Ac—D-Asn) | D-Aph(Ac—D-Asn) | " |
| 22 | Aph(Ac—D-Cit) | D-Aph(Ac—D-Cit) | " |
| 23 | Aph(Ac—Gly) | D-Aph(Ac—Gly) | " |
| 24 | Aph(Ac—His) | D-Aph(Ac—His) | Gly—NH₂ |
| 25 | Aph(Ac—Gln) | D-Aph(Ac—Gln) | NHCH₂CH₃ |
| 26 | Aph(Ac—Thr) | D-Aph(Ac—Thr) | to |
| 27 | Aph(Ac—Tyr) | D-Aph(Ac—Tyr) | AzaGly—NH₂ |

For example, the peptide No. 20 is synthesized by making the intermediate as described in Example 1 and deprotecting the side chains of Aph by removing the Fmoc groups again using 20% piperidine in DMF. After washing, the amino groups on the side chains are caused to react by treating with Boc-D-His(Tos), about 2 millimole, in a DCM:DMF solvent mixture with a suitable coupling agent such as DIC. After about 2 hours at room temperature, the coupling should be complete. The Boc group is then removed using TFA, and acetylation of the α-amino group of D-His is carried out using a large excess of acetic anhydride in a mixture of DCM:DMF for about 15 minutes. After washing, the peptide is cleaved from the resin and purified as described hereinbefore.

The peptides listed in Table B are considered effective to block GnRH-induced LH secretion in vitro at a reasonable concentration. All of the peptides are considered to be effective to prevent ovulation of female mammals at low dosages.

EXAMPLE 4

The following peptides indicated in Table C, having the general formula:

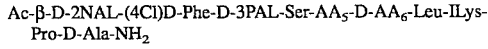

Ac-β-D-2NAL-(4Cl)D-Phe-D-3PAL-Ser-AA₅-D-AA₆-Leu-ILys-Pro-D-Ala-NH₂ are prepared by the solid-phase procedure generally referred to in Example 1.

TABLE C

| No. | AA₅ | AA₆ |
|---|---|---|
| 28 | Aph(Iac) | D-Aph(Iac) |
| 29 | Aph(Ura) | D-Aph(Ura) |
| 30 | Aph(Iop) | D-Aph(Iop) |
| 31 | Aph(Atc) | D-Aph(Atc) |
| 32 | Ahp(Pca) | D-Ahp(Pca) |
| 33 | Aph(Pca) | D-Aph(Pca) |
| 34 | Aph(Ac) | D-Aph(Ac) |
| 35 | Aph(For) | D-Aph(For) |
| 36 | Aph(Pr) | D-Aph(Pr) |
| 37 | Aph(Bt) | D-Aph(Bt) |
| 38 | Aph(Cac) | D-Aph(Cac) |
| 39 | Aph(Hac) | D-Aph(Hac) |

The decapeptide-resin intermediate is prepared as described hereinbefore and the Fmoc protecting groups are removed from the 5- and 6-position residues. For example, to synthesize peptide No. 32, the deprotected peptide resin is treated with Pca which has been activated by the formation of its pentafluorophenylester. More specifically, 248 milligrams (2 mm.) of 2-pyrazine carboxylic acid is dissolved in 40 ml. of DMF to which 368 mg. of pentafluorophenyl(2 mM) and 252 mg. of DIC(2 mM) are added. After stirring the mixture at room temperature for 30 minutes, it is added to the deblocked resin and the final mixture is agitated at room temperature for about 12 hours to complete the coupling. After washing, the peptide resin is dried and then the peptide is cleaved by treating with Hf at 0° C. for about 1.5 hours using anisole (2 ml.) as a scavenger. After removal of Hf under vacuum, the resin is washed with ethylether and then extracted with a mixture of 25% $CH_3CN$ and 75% $H_2O$. Purification is carried out as described hereinbefore.

The peptides listed in Table C are considered effective to block GnRH-induced LH secretion in vitro at a reasonable concentration. All of the peptides are considered to be effective to prevent ovulation of female mammals at low dosages.

EXAMPLE 5

Peptides as indicated in TABLE D having the formula:

Ac-β-D-2NAL-(4Cl)D-Phe-D-3PAL-Ser-$AA_5$-$AA_6$-$AA_7$-ILys-Pro-$AA_{10}$ are prepared using the general solid-phase procedure described in Example 1, but interrupting the chain elongation after adding the position-6 residue to acylate its side chain.

TABLE D

|    | $AA_5$  | $AA_6$   | $AA_7$ | $AA_{10}$            |
|----|---------|----------|--------|----------------------|
| 40 | Aph(atz)| D-Aph(Ac) | Leu   | D-Ala—$NH_2$         |
| 41 | Aph(atz)| D-Aph(Acr)| NML   | $NHCH_2CH_3$         |
| 42 | Aph(atz)| D-Aph(For)| NML   | D-Ala—$NH_2$         |
| 43 | Aph(atz)| D-Aph(Bt) | Leu   | Gly—$NH_2$           |
| 44 | Ahp(atz)| D-Aph(Cac)| NML   | D-Ala—$NH_2$         |

For example, peptide No. 40 is synthesized by interrupting the chain elongation after adding the first 5 residues to the MBHA resin and removing the side chain Fmoc protecting group from D-Aph using piperidine in DMF as described hereinbefore. The acetylation of the side chain amino group is then carried out using an excess of acetic anhydride in DMF. Following washing, the Boc protecting group is removed using TFA and the chain elongation synthesis is continued as before. Following completion of the decapeptide, the protecting group at the N-terminus is removed, acetylation is carried out, and then the creation of the triazole moiety at the side chain of the 5-position is carried out as described in Example 1, using proportionately less amounts of reactants inasmuch as only one residue in the chain has a side chain that is undergoing reaction. Alternatively, the creation of the triazole group is carried out any time after the addition of Aph(Fmoc) to the growing peptide chain. Cleavage and purification are also carried out as described generally in Example 1.

The peptides listed in Table D are considered effective to block GnRH-induced LH secretion in vitro at a reasonable concentration. All of the peptides are considered to be effective to prevent ovulation of female mammals at low dosages. Peptide No. 40 exhibits very long duration of bioactivity, suppressing LH secretion to a level of less than about 20% of original concentration in peripheral serum for more than 72 hours.

EXAMPLE 6

Peptides as indicated in TABLE E having the formula:

G-$AA_1$-(A)D-Phe-$AA_3$-Ser-Aph(β-Ala)(atz)-D-Aph(β-Ala)(atz)-$AA_7$-ILys-Pro-$AA_{10}$ are prepared by the solid-phase procedure generally referred to above.

TABLE E

| No. | G   | $AA_1$       | A       | $AA_3$      | $AA_7$ | $AA_{10}$       |
|-----|-----|--------------|---------|-------------|--------|-----------------|
| 45  | Ac  | D-Trp        | 4F      | D-Trp       | Leu    | D-Ala—$NH_2$    |
| 46  | Acr | $6NO_2$D-Trp | 4Cl     | βD-2NAL     | NML    | Gly—$NH_2$      |
| 47  | For | $Me_5$D-Phe  | 4Br     | 6FD-Trp     | NML    | $NHCH_2CH_3$    |
| 48  | Bz  | 4FD-Phe      | $4NO_2$ | ForD-Trp    | Leu    | Gly—$NH_2$      |
| 49  | Acr | βD-LNAL      | $4CH_3$ | $6NO_2$D-Trp| NML    | AzaGly—$NH_2$   |
| 50  | Ac  | 4ClD-Phe     | H       | βD-LNAL     | Nle    | D-Ala—$NH_2$    |
| 51  | Bz  | βD-2NAL      | $4OCH_3$| D-3PAL      | Trp    | Gly—$NH_2$      |
| 52  | Acr | $4NO_2$D-Phe | 4F      | βD-1NAL     | Phe    | D-Ala—$NH_2$    |
| 53  | Ac  | βD-2AL       | $2,4Cl_2$| AcD-Trp    | Nva    | $NHCH_2CH_3$    |
| 54  | For | $4CH_3$D-Phe | 4F      | $6CH_3$D-Trp| Nle    | Gly—$NH_2$      |
| 55  | Ac  | 6ClD-Trp     | 4Br     | 6ClD-Trp    | 3PAL   | D-Ala—$NH_2$    |
| 56  | Acr | 6FD-Trp      | 4F      | D-2PAL      | Met    | AzaGly—$NH_2$   |

The peptides listed in Table E are considered effective to block GnRH-induced LH secretion in vitro at a reasonable concentration. All of the peptides are considered to be effective to prevent ovulation of female mammals at low dosages.

Results of in vivo testing of selected of these antagonists are shown in the following Table X, with the dosages being given in micrograms:

TABLE X

| Peptide No. | Dosage | Rats Ovulating | Dosage | Rats Ovulating |
|-------------|--------|----------------|--------|----------------|
| 1           | 1.0    | 5/8            | 0.5    | 3/4            |
| 2           | 1.0    | 9/18           | 2.5    | 0/3            |
| 3           | 1.0    | 1/8            | 0.5    | 4/6            |
| 4           | 1.0    | 1/8            | 0.5    | 4/4            |
| 5           | 1.0    | 2/8            |        |                |
| 6           | 1.0    | 0/2            | 0.5    | 6/6            |
| 10          | 1.0    | 8/12           |        |                |
| 15          | 2.5    | 4/8            | 1.0    | 2/2            |
| 16          | 1.0    | 4/5            |        |                |
| 17          | 1.0    | 4/7            | 2.5    | 1/9            |
| 18          | 2.5    | 2/5            |        |                |
| 19          | 1.0    | 2/7            |        |                |
| 20          | 2.5    | 0/2            | 1.0    | 4/15           |
| 21          | 1.0    | 4/6            | 2.5    | 2/8            |
| 22          | 2.5    | 4/8            | 1.0    | 6/7            |
| 23          | 1.0    | 5/8            | 0.5    | 3/4            |
| 28          | 1.0    | 3/8            | 0.5    | 3/3            |
| 29          | 1.0    | 4/8            | 0.5    | 4/4            |
| 31          | 1.0    | 11/15          | 0.5    | 4/4            |
| 33          | 1.0    | 4/8            | 0.5    | 8/8            |
| 34          | 1.0    | 5/15           | 0.5    | 6/7            |
| 40          | 1.0    | 2/7            | 2.5    | 0/8            |

Following purification of the peptides, various of them are further characterized by subjection to high performance liquid chromatography on $C_{18}$ silica (Vydac 0.46×25 cm) using a flow rate of 1.7 ml/min and a gradient of from 35% to 85% by volume of Buffer B over a time span of 50 minutes, with the remainder being Buffer A. Buffer A is a solution of 0.3% triethylamine (v/v) and 0.1% phosphoric acid in water at pH 7.0; Buffer B is 60% by volume acetonitrile and 40% by volume Buffer A. The following Table Y shows when the specific peptides elute from the $C_{18}$ silica having a particle size of about 5μ and a pore size of 300 Å when subjected to the stated gradient over 50 minutes:

TABLE Y

| Peptide No | Time of Elution | Optical Rotation $[\alpha_D]$* |
|---|---|---|
| 1 | 13.9 | −34° |
| 2 | 14.3 | −31° |
| 3 | 14.7 | −33° |
| 4 | 15.2 | −41° |
| 5 | 15.2 | −30° |
| 6 | 16.5 | |
| 10 | 13.0 | −36° |
| 15 | | −46° |
| 16 | 16.1 | −29° |
| 17 | 15.5 | −48° |
| 18 | 16.1 | −33° |
| 19 | 15.4 | −18° |
| 20 | 15.8 | −31° |
| 21 | 14.6 | −25° |
| 22 | 14.3 | −24° |
| 23 | 16.6 | −39° |
| 28 | 17.0 | −32° |
| 29 | 18.2 | −26° |
| 31 | 15.5 | −32° |
| 33 | 23.5 | −31° |
| 34 | 19.9 | −38° |
| 40 | 17.9 | −26° |

*C = 1 in 50% acetic acid, corrected for presence of $H_2O$ and TFA

EXAMPLE 7

Peptides as indicated in TABLE F having the formula:

pGlu-His-Trp-Ser-Tyr-$AA_6$-$AA_7$-Arg-Pro-$AA_{10}$ are prepared by the solid phase procedures as generally referred to hereinbefore.

TABLE F

| | $AA_6$ | $AA_7$ | $AA_{10}$ |
|---|---|---|---|
| 57 | D-Aph(Gly)(atz) | Leu | Gly—$NH_2$ |
| 58 | D-Aph(β—Ala)(atz) | " | " |
| 59 | D-Aph(Gab)(atz) | " | " |
| 60 | D-Aph(Ahx)(atz) | " | " |
| 61 | D-Aph(Ser)(atz) | " | AzaGly—$NH_2$ |
| 62 | D-Aph(Ser) | " | $NHCH_2CH_3$ |
| 63 | D-Aph(Gly)(atz) | " | " |
| 64 | D-Aph(Ac—Ser) | " | " |
| 65 | D-Aph(Ura) | NML | " |
| 66 | D-Aph(Ac—D-His) | " | " |
| 67 | D-Aph(Iac) | Leu | Gly—$NH_2$ |
| 68 | D-Aph(Ac—Gly) | " | $NHCH_2CH_3$ |
| 69 | D-Aph(For) | " | " |
| 70 | D-Aph(Ac) | " | " |
| 71 | D-Aph(Pr) | NML | AzaGly$NH_2$ |
| 72 | D-Aph(Cac) | " | $NHCH_2CH_3$ |
| 73 | D-Aph(Bt) | " | $NHCH_3$ |
| 74 | D-Aph(Hac) | Leu | $NHCH_2CH_2CH_3$ |
| 75 | D-Aph(Acr) | " | Gly—$NH_2$ |
| 76 | D-Ahp(Ac) | " | " |
| 77 | D-Aph(Gly)(atz) | NML | " |

TABLE F-continued

| | $AA_6$ | $AA_7$ | $AA_{10}$ |
|---|---|---|---|
| 78 | D-Aph(Ac—Ser) | " | $NHCH_2CH_3$ |

The peptides described in TABLE F are considered to be effective to cause the release of LH and FSH in female rats. All of them are considered to be substantially more effective than native GnRH.

An exemplary synthesis of Peptide No. 70 which has the formula pGlu-His-Trp-Ser-Tyr-D-Aph(Ac)-Leu-Arg-Pro-NHCH$_2$CH$_3$ is set forth hereinafter.

An N$^\alpha$-ethylamino methyl resin is used, and Boc-protected Pro is coupled to the resin over a 2-hour period in $CH_2Cl_2$ using a 3-fold excess of Boc derivative and DCC as an activating reagent. The Pro residue attaches by an amide bond to the secondary amino group on the resin.

Following the coupling of each amino acid residue, washing, deblocking and coupling of the next amino acid residue is carried out in accordance with the schedule set forth hereinbefore, using an automated machine and beginning with about 5 grams of resin. The side chain primary amino group of D-Aph in the 6-position is protected by Fmoc. Bzl(benzyl ether) is used as a side chain protecting group for the hydroxyl group of Ser, and 2,6-dichlorobenzyl is used as the side chain protecting group for the hydroxyl group of Tyr. Boc-Arg(Tos) is used for the 8-position, and Boc-His(Tos) is used for the 2-position. pGlu at the N-terminus is introduced as Z-pGlu or as plain pGlu, as desired.

Following completion of the assembly of the peptide, the following intermediate is present:

(Z)pGlu-His(Tos)-Trp-Ser(Bzl)-Tyr(DCB)-D-Aph(Fmoc)-Leu-Arg-(Tos)-Pro-N(Et)-[ resin support].

The side chain of the D-Aph residue in the 6-position is then deprotected. The Fmoc protecting group is removed by treatment of the peptidoresin with 20 percent piperidine in DMF for 5 minutes, then washing with DMF, then treatment with more piperidine/DMF for 20 minutes. After washing the resin with DMF, $CH_3OH$, $CH_2Cl_2$, and finally DMF, the newly freed amino group is treated with a large excess of acetic anhydride in a mixture of DCM:DMF for about 15 minutes. The peptidoresin is then washed as before.

The cleavage of the peptide from the resin and deprotection of the pGlu, His, Ser, Tyr and Arg side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by high performance liquid chromatography (HPLC), as known in the art and specifically set forth in J. Rivier, et al. *J. Chromatography,* 288 (1984) 303–328.

The peptide is judged to be homogeneous using capillary zone electrophoresis (CZE), as well as by using reversed-phase high performance liquid chromatography and an aqueous triethylammonium phosphate solution plus acetonitrile. Amino acid analysis of the resultant, purified peptide is consistent with the formula for the prepared structure, showing substantially integer-values for each amino acid in the chain; mass spectral analysis is also consistent. Biological testing in vivo shows good biological activity in causing the release of LH and FSH in female rats.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously. Oral dosages might be higher; however, the nature of these compounds should permit effective oral administration. Overall, treatment of subjects with these peptides is generally carried out in the same manner as the clinical treatment using other antagonists of GnRH using a suitable carrier in which the peptide is soluble.

It may also be desirable to deliver the GnRH analog over prolonged periods of time, for example, for periods of one week to one year from a single administration, and slow release, depot or implant dosage forms may be utilized. For example, a suitable, slow-release depot formulation for injection may contain the GnRH antagonist or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemotherapy. They are also useful for treatment of steroid-dependent tumors. Effective dosages will vary with the form of administration and the particular species of mammal being treated. An example of one typical dosage form is a bacteriostatic water solution at a pH of about 6 containing the peptide which solution is administered parenterally to provide a dose in the range of about 0.1 to 2.5 mg/kg of body weight per day. These compounds are considered to be well-tolerated in vivo and to resist gelling; accordingly, they are considered to be particularly well-suited for administration by subcutaneous injection in a bacteriostatic water solution at appropriate concentrations, above about 0.75 mg/ml and even above about 1.0 mg/ml, without danger of gelling at the point of injection.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. Instead of creating the preferred amide bond in the side chain by linking a moiety having a carboxyl group to an amino group on the residue in the peptide chain, a carboxyl group can be attached to the Phe residue and thereafter linked to the modifying moiety which contains a primary amino group. D-2PAL and D-4PAL are considered to be equivalents of D-3PAL. Other equivalent acylating groups can be used instead of acetyl at the N-terminus. Substituted Phe, such as (4F)Phe, can be used instead of Phe in the 7-position. Har is considered the equivalent of Arg in the 8-position, and both butyl Lys and diethyl Lys are considered to be equivalents of ILys. However, ILys is most preferred. Other hydrophobic amino acid residues can also be employed in the 1-position, preferably in D-isomer form, and are considered equivalents of those specified. Moreover, the antagonists can be administered in the form of their pharmaceutically or vetinarially acceptable, nontoxic salts, as indicated hereinbefore, which are considered equivalents.

Particular features of the invention are emphasized in the claims which follow.

What is claimed is:

1. A GnRH antagonist peptide, or a nontoxic salt thereof, having the formula:

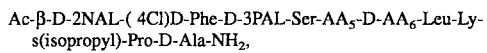

Ac-β-D-2NAL-(4Cl)D-Phe-D-3PAL-Ser-AA$_5$-D-AA$_6$-Leu-Lys(isopropyl)-Pro-D-Ala-NH$_2$, wherein AA$_5$ and AA$_6$ are independently a residue of a modified Phe having a substitution in the phenyl ring thereof, said substitution of at least one of AA$_5$ and AA$_6$ being an amino group that is acylated by an acyl group having 5 or less carbon atoms.

2. A GnRH antagonist peptide according to claim 1 wherein both AA$_5$ and AA$_6$ have amino groups which are acylated by acetyl or chloroacetyl.

3. A GnRH antagonist peptide according to claim 1 wherein said acyl group has the formula:

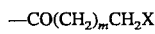

—CO(CH$_2$)$_m$CH$_2$X where m is 0, 1, 2 or 3 and X is H, Cl, F, Br or I.

4. A GnRH antagonist peptide according to claim 3 wherein X is H or Cl.

5. A GnRH antagonist peptide, or a nontoxic salt thereof, having the formula:

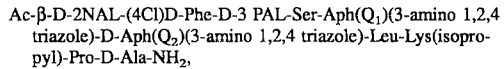

Ac-β-D-2NAL-(4Cl)D-Phe-D-3 PAL-Ser-Aph(Q$_1$)(3-amino 1,2,4 triazole)-D-Aph(Q$_2$)(3-amino 1,2,4 triazole)-Leu-Lys(isopropyl)-Pro-D-Ala-NH$_2$, where Q$_1$ and Q$_2$ are independently amino acids selected from the group consisting of Gly, β-Ala, Gab and the D- and L-isomers of Ala, Ahx and Ser.

6. A GnRH antagonist peptide according to claim 5 wherein Q$_1$ and Q$_2$ are Gly.

7. A GnRH antagonist peptide according to claim 5 wherein Q$_1$ and Q$_2$ are β-Ala.

8. A GnRH antagonist peptide, or a nontoxic salt thereof, having the formula:

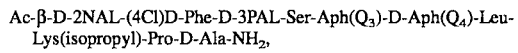

Ac-β-D-2NAL-(4Cl)D-Phe-D-3PAL-Ser-Aph(Q$_3$)-D-Aph(Q$_4$)-Leu-Lys(isopropyl)-Pro-D-Ala-NH$_2$, where Q$_3$ consists of a substituted or unsubstituted unsaturated heterocylic ring moiety having from 2 to 4 nitrogen atoms, and wherein Q$_4$ comprises an unsaturated heterocylic ring moiety having from 2 to 4 nitrogen atoms, or an acyl group having 5 or less carbon atoms, provided however that at least one of $Q_3$ and $Q_4$ is connected to said Aph side chain by an amide linkage.

9. A GnRH antagonist peptide according to claim 8 having the formula:

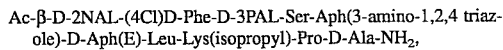

Ac-β-D-2NAL-(4Cl)D-Phe-D-3PAL-Ser-Aph(3-amino-1,2,4 triazole)-D-Aph(E)-Leu-Lys(isopropyl)-Pro-D-Ala-NH$_2$, where E is an acyl group having 5 or less carbon atoms.

10. A GnRH antagonist peptide according to claim 9 wherein E is acetyl.

11. A GnRH antagonist peptide, or a nontoxic salt thereof, which is effective to suppress LH secretion for more than 72 hours following administration and which has the formula:

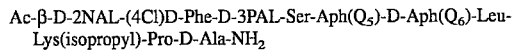

Ac-β-D-2NAL-(4Cl)D-Phe-D-3PAL-Ser-Aph(Q$_5$)-D-Aph(Q$_6$)-Leu-Lys(isopropyl)-Pro-D-Ala-NH$_2$ wherein $Q_5$ is selected from the group consisting of For, Ac, 3-amino-1,2,4 triazole, β-Ala(3-amino-1,2,4 triazole) and Gab(3-amino-1,2,4 triazole) and $Q_6$ is selected from the group consisting of For, Ac, β-Ala(3-amino-1,2,4 triazole) and Gab(3-amino-1,2,4 triazole).

12. A GnRH antagonist peptide according to claim 11 wherein $Q_5$ and $Q_6$ are Gab(3-amino-1,2,4 triazole).

13. A GnRH antagonist peptide according to claim 11 wherein $Q_5$ and $Q_6$ are both Ac.

14. A GnRH antagonist peptide according to claim 11 wherein $Q_5$ and $Q_6$ are both For.

15. A method for inhibiting the secretion of gonadotropins in mammals comprising administering to a mammal an effective amount of a GnRH antagonist peptide or a nontoxic salt thereof as defined in claim 11, which is effective to substantially decrease LH and FSH levels.

* * * * *